United States Patent
Rastogi et al.

(10) Patent No.: US 10,660,868 B2
(45) Date of Patent: May 26, 2020

(54) MODIFIED RELEASE FORMULATIONS OF MEMANTINE ORAL DOSAGE FORMS

(71) Applicant: Forest Laboratories Holdings Limited, Hamilton (BM)

(72) Inventors: Suneel K Rastogi, Island Park, NY (US); Niranjan Rao, Belle Mead, NJ (US); Antonia Periclou, Jersey City, NJ (US); Wattanaporn Abramowitz, West Windsor, NJ (US); Mahendra G Dedhiya, Pomona, NY (US); Shashank Mahashabde, Kendall Park, NJ (US)

(73) Assignee: Forest Laboratories Holdings Limited, Hamilton (BM)

( * ) Notice: Subject to any disclaimer, the term of this patent is extended or adjusted under 35 U.S.C. 154(b) by 0 days.

(21) Appl. No.: 15/215,456

(22) Filed: Jul. 20, 2016

(65) Prior Publication Data

US 2016/0324803 A1    Nov. 10, 2016

Related U.S. Application Data

(63) Continuation of application No. 14/607,526, filed on Jan. 18, 2015, now abandoned, which is a continuation of application No. 14/228,944, filed on Mar. 28, 2014, now abandoned, which is a continuation of application No. 13/948,438, filed on Jul. 23, 2013, now abandoned, which is a continuation of application No. 13/618,014, filed on Sep. 14, 2012, now abandoned, which is a continuation of application No. 13/233,381, filed on Sep. 15, 2011, now abandoned, which is a continuation of application No. 11/155,330, filed on Jun. 16, 2005, now Pat. No. 8,039,009.

(60) Provisional application No. 60/581,242, filed on Jun. 17, 2004.

(51) Int. Cl.
*A61K 31/13* (2006.01)
*A61K 9/20* (2006.01)
*A61K 47/38* (2006.01)
*A61K 9/00* (2006.01)

(52) U.S. Cl.
CPC ............ *A61K 31/13* (2013.01); *A61K 9/0053* (2013.01); *A61K 9/2009* (2013.01); *A61K 9/2013* (2013.01); *A61K 9/2018* (2013.01); *A61K 9/2054* (2013.01); *A61K 9/2077* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 6,194,000 B1 * | 2/2001 | Smith | A61K 9/5084 424/422 |
| 2005/0191349 A1 * | 9/2005 | Boehm | A61K 9/2013 424/464 |
| 2005/0232990 A1 * | 10/2005 | Boehm | A61K 9/0095 424/464 |

* cited by examiner

*Primary Examiner* — Jared Barsky
(74) *Attorney, Agent, or Firm* — Roy Issac

(57) ABSTRACT

The present invention provides pharmaceutical compositions given once daily containing at least one therapeutically active ingredient selected from the group consisting of memantine and a pharmaceutically acceptable salt of memantine, and a pharmaceutically acceptable polymeric matrix carrier. The dosage forms of the invention sustain the release of the therapeutically active agent from about 4 to about 24 hours when said dosage form is exposed to aqueous solutions. following entry of said form into a use environment, wherein said dosage form has a dissolution rate of more than about 80% after passage of about 6 hours to about 12 hours following said entry into said use environment.

8 Claims, 10 Drawing Sheets

MODIFIED RELEASE FORMULATIONS OF MEMANTINE ORAL DOSAGE FORMS

CROSS-REFERENCE TO RELATED APPLICATIONS

This application claims priority under 35 U.S.C. § 119, based on U.S. Provisional Application Ser. No. 60/581,242 filed Jun. 17, 2004, which is hereby incorporated by reference in its entirety.

FIELD OF THE INVENTION

The present invention is directed to pharmaceutical solid, oral dosage forms which exhibit a modified release profile. The invention is particularly suitable for once-a-day solid oral pharmaceutical dosage forms in which the active ingredient is memantine, releasing a therapeutically effective amount of the active ingredient over an extended time period.

BACKGROUND OF THE INVENTION

Solid oral drug compositions or preparations have various release profiles such as a modified or extended release profile as referenced by USP XXIII (CDER, FDA, Rockville, Md.) or an immediate release profile as referenced by FDA guidelines (Dissolution Testing of Immediate Release Solid Oral Dosage Forms, issued August 1997, Section IV-A). For example, in the dissolution testing guideline for modified release profiles, material dissolves over an extended period and its dissolution is measured over time. A minimum of three time points is recommended and should cover early, middle and late stages of the dissolution profile. The last measurement should be at a time point where at least 80% of the drug is dissolved (Guidance for Industry, "Extended Release Oral Dosage Forms: Development, Evaluation, and Application of In Vitro/In Vivo Correlations", Food and Drug Administration, CDER, September 1997, Page 17). Adequate sampling should be performed, for example, at 1, 2 and 4 hours and every two hours thereafter until 80% of the drug is released (Guidance for Industry, SUPAC-MR: Modified Release Solid Oral Dosage Forms," Food and Drug Administration, CDER, September 1997, Page 6). The preferred dissolution apparatus is USP apparatus I (basket) or II (paddle), used at compendially recognized rotation speeds, e.g., 100 rpm for the basket and 50-75 rpm for the paddle (Guidance for Industry, "Extended Release Oral Dosage Forms: Development, Evaluation, and Application of In Vitro/In Vivo Correlations", Food and Drug Administration, CDER, September 1997, Page 4).

Modified release solid oral dosage forms permit the sustained release of the active ingredient over an extended period of time in an effort to maintain therapeutically effective plasma levels over similarly extended time intervals and/or to modify other pharmacokinetic properties of the active ingredient. Immediate release solid dosage forms permit the release of most or all of the active ingredient over a short period of time, such as 60 minutes or less, and make rapid absorption of the drug possible. A multiphase release profile (i.e., a composition containing at least an immediate release formulation and at least one modified release formulation) may be employed to attain one or more combinations of release rates to attain more specific therapeutic objectives such as a portion of drug releasing immediately, followed by an extended release. However, modulation of the release rate of an active ingredient does not necessarily ensure that long-lasting effective blood level concentrations will be consistently achieved or that the pharmacological effect will be based solely on the release of the drug.

Sustained release formulations for drugs have become increasingly available. This is true especially when the particular drug is relatively soluble. Various formulation techniques have been used for providing a sustained release formulation of soluble drugs. In many such formulations, a drug-containing particle is coated by one or more release retardant layers or films or is dispersed within a continuous matrix such as a polymeric matrix. The coating layer or the matrix comprises a relatively insoluble material or materials, and the release of the drug is controlled by means of the resistance of the coating layer or matrix against the diffusion of the drug there through. The release of the drug from such formulations is driven, e.g., by the gradient of the drug concentration resulting from penetration of, e.g., gastric fluid, by diffusion into the formulation.

One or more film-forming polymers may be employed to provide sustained release of the active substance by controlling its rate of diffusion across the film barrier(s). However, such an approach is compromised if, during ingestion of the oral dosage form, the film is prematurely breached, as by chewing, splitting or abrasion, thereby releasing an excessive amount of active ingredient, which can result in undesirable effects from excessive single-shot drug release, and in failure of the dosage form to remain effective for the required duration.

In the more common matrix-controlled release approach, lipophilic substances, e.g., higher alcohols, waxes, or insoluble thermoplastic materials, are employed. The release is controlled by the rate of diffusion of the active ingredient into the surrounding medium and, if the matrix itself is degradable, by the rate of its degradation. One of the disadvantages is that a complete release of drug from the matrix is frequently not achieved in practice. Another drawback is that dose proportionality of the dosage forms is not readily achieved, thus, requiring different compositions for different strengths. Thus, the matrix composition to formulate a 20 mg sustained release dosage form may well be different from the matrix composition to formulate a 40 mg sustained release dosage form.

U.S. Pat. No. 5,382,601 provides solid pharmaceutical dosage forms containing memantine, which exhibit an extended two-phase release profile, with a portion of the drug being released immediately, followed by a sustained release of the remainder. The matrix of this formulation contains both a water-soluble and a water-insoluble salt of casein, preferably sodium and calcium caseinate. However, casein has an unpleasant taste; it is associated with undesirable effect of exacerbating some side effects as disclosed in U.S. Pat. No. 6,413,556; and displays instability in varying pH. Another concern regarding casein is the possibility of Bovine Spongiform Encephalitis (BSE) contamination since casein is an animal-derived milk protein.

A general method of modified release for N-methyl-D-aspartate (NMDA) receptor antagonists was described in U.S. Pat. No. 6,194,000. This method also involves preparing an instant release component and a modified release component to arrive at the final formulation. The patent discloses a pellet (not a bead) consisting of a coated core, the coating being any suitable coating using organic solvent-based systems. However, not all NMDA antagonists act in the same manner, and this patent does not specifically disclose compositions containing memantine.

Currently, a dosing regimen of memantine of twice a day is employed using immediate release tablets. This may be undesirable because patient compliance decreases as the frequency of taking a drug increases. Moreover, administration of an immediate-release tablet can lead to greater frequency of adverse events due to a faster rate of absorption. For pain treatment, it is very important to maintain the pain relief without additional discomfort. There is therefore an existing and continual need for a once a day modified release formulation containing memantine or a pharmaceutically acceptable salt of memantine with reliable slower absorption over a targeted period of time.

SUMMARY OF THE INVENTION

According to the present invention, it has now been found that memantine, and its salts, including the hydrochloride salt as well as other pharmaceutically acceptable salts of memantine can be formulated into a modified release form with anticipated improvements in tolerability. The formulation of the present invention includes memantine or a pharmaceutically acceptable salt thereof, a pharmaceutically acceptable polymeric carrier (coating and/or matrix) that substantially contributes to the modification of the release of memantine, and one or more excipients to be administered in a once-a-day oral dosage form.

Specifically, the present invention provides a dosage form which slowly releases the active agent at a release rate of from at least about 70% to about 80% in about 4 hours to about 24 hours following entry of the dosage form into a use environment. In one embodiment, the dosage form is released to this extent over 6 hours from entry into the use environment, e.g., the gastric fluids. Alternatively, the dosage form is released to this extent over 12 hours from entry into the use environment.

For a 12-hour release formulation, at least 70%, preferably at least 80% of the active ingredient, e.g., memantine hydrochloride, is released after about 12 hours following entry into the use environment, but not before such time. In the 12-hour oral dosage form of the present invention, the active ingredient is usually present in amounts from about 1.0% w/w to about 20.0% w/w, preferably from about 1.6% w/w to about 20.0% w/w, most preferably from about 2.5% w/w to about 20% w/w. Alternatively, the active ingredient may be measured as mg per tablet, ranging from about 5 to about 80 mg per tablet. Preferably, the tablets contain 7 mg, 10 mg, 20 mg, 28 mg, 40 mg or 80 mg active ingredient. Alternatively, the active ingredient in the use of seeds may be up to 100 mg.

For a 6-hour release formulation, at least 70% preferably at least 80% of the active ingredient is released after about 6 hours following entry into the use environment, but not before such time. In the 6-hour oral dosage form of the present invention, the active ingredient is usually present in amounts from about 1.0% w/w to about 35% w/w, preferably from about 1.6% w/w to about 35.0% w/w, most preferably from about 5.0% w/w to about 35.0% w/w. The active ingredient would therefore be present from about 5 mg to about 80 mg per tablet. Preferably, the tablets contain 7 mg, 10 mg, 20 mg, 28 mg, 40 mg, or 80 mg active ingredient.

In one embodiment of the present invention, the polymeric carrier is a polymeric matrix. Preferably, the polymeric matrix is a swellable matrix that contains hydroxypropyl methylcellulose. The hydroxypropyl methylcellulose, in 12-hour formulations is present in amounts from about 50% w/w to about 80% w/w, more preferably in amounts from about 68% w/w to about 77% w/w. In 6-hour formulations, the hydroxypropyl methylcellulose is present in amounts from about 20% w/w to about 70% w/w, preferably from about 54% w/w to about 65% w/w.

The formulations of the present invention may further comprise a filler. In one embodiment, the dosage forms contain the lactose monohydrate as filler. In 12-hour formulations, the lactose monohydrate is present in amounts from about 5% w/w to about 50% w/w, more preferably from about 5% w/w to about 25% w/w, most preferably from about 6.9% w/w to about 15% w/w. In 6-hour formulations, the lactose monohydrate is present in amounts from about 5% w/w to about 80% w/w, more preferably from about 5% w/w to about 71% w/w, most preferably from about 7% w/w to about 24% w/w.

In another embodiment, the dosage forms contain the microcrystalline cellulose as filler in amounts from about 5% w/w to about 80% w/w, more preferably from about 5% w/w to about 71% w/w, most preferably from about 7% w/w to about 40% w/w.

In yet another embodiment, the dosage forms contain the dicalcium phosphate dihydrate as filler in amounts from about 5% w/w to about 80% w/w, more preferably from about 5% w/w to about 71% w/w, most preferably from about 7% w/w to about 40% w/w.

The formulations of the present invention may further comprise a lubricant, preferably magnesium stearate. In 12-hour formulations, the magnesium stearate is present in amounts ranging from about 0.8% w/w to about 1.2% w/w, preferably from about 0.9% w/w to about 1.1% w/w. In 6-hour formulations, the magnesium stearate is present in amounts ranging from about 0.4% to about 0.6% w/w, preferably in an amount of about 0.5% w/w.

The formulations of the present invention may also contain one or more additional carriers, excipients, fillers, stabilizing agents, binders, colorants, glidants and lubricants.

DETAILED DESCRIPTION OF THE INVENTION

Figure 1:
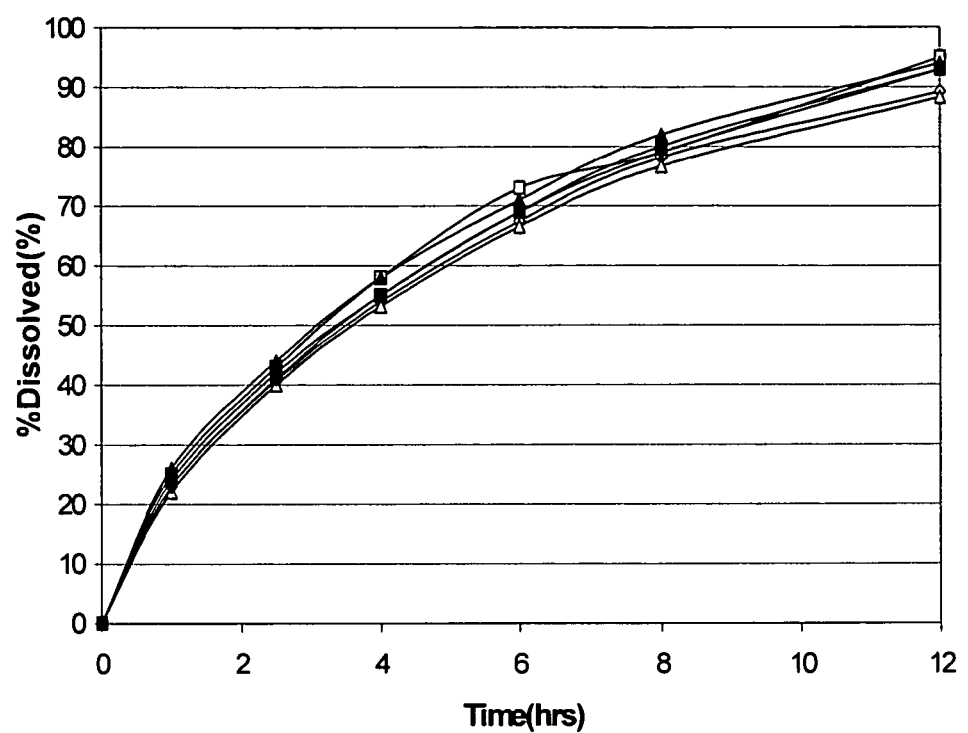
FIG. 1 shows the dissolution rates for the scaled up batches of 10, 20, and 40 mg memantine HCL tablets after six months of storage conditions at 40° C./75% RH. Dissolution is shown as percent dissolved over time (hours). The open diamond represents the 40 mg strength; the open square represents the 20 mg strength; and the open triangle represents the 10 mg strength. These open shapes represent measurements at 6 months. The corresponding filled shapes represent the baseline measurements.

In accordance with the present invention, a pharmaceutical composition is provided for the once-daily administration of memantine or a pharmaceutically acceptable salt thereof, preferably its HCl salt, or derivatives thereof, to a human or animal, where the composition includes memantine in oral solid dosage forms, preferably tablets.

In the present invention, the pharmaceutical compositions comprise a therapeutically effective amount of memantine free base or a pharmaceutically acceptable salt thereof, preferably the HCl salt, one or more release modifiers in the form of polymeric coatings and matrices, as well as, optionally, one or more carriers, excipients, anti-adherants, fillers, stabilizing agents, binders, colorants, glidants, and lubricants (all pharmaceutically acceptable).

Memantine (1-amino-3,5-dimethyladamantane), which is an analog of 1-amino-cyclohexane (disclosed, e.g., U.S. Pat. Nos. 4,122,193; 4,273,774; 5,061,703), is a systemically-active uncompetitive NMDA receptor antagonist having low to moderate affinity for the receptor and strong voltage dependency and rapid blocking/unblocking kinetics. These pharmacological features allow memantine to block sustained activation of the receptor under pathological conditions and to rapidly leave the NMDA channel during normal physiological activation of the channel. Memantine and pharmaceutically acceptable salts thereof (e.g., the HCl salt, MW 215.77) is approved in the U.S. for treatment of Alzheimer's disease. Approval of memantine is currently sought for the indication of neuropathic pain (wherein memantine has demonstrated activity in in vitro models), and is currently approved outside the United States as an oral formulation for both Alzheimer's and Parkinson's Disease.

According to the invention, memantine may be used in the form of a free base or a pharmaceutically acceptable salt. Suitable salts of the compound include, but are not limited to, acid addition salts, such as those made with hydrochloric, methylsulfonic, hydrobromic, hydroiodic, perchloric, sulfuric, nitric, phosphoric, acetic, propionic, glycolic, lactic pyruvic, malonic, succinic, maleic, fumaric, maleic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid. In a preferred embodiment, the salt is memantine hydrochloride ($C_{12}H_{21}N \cdot HCl$, MW 215.77). The term "salts" can also include addition salts of free acids or free bases. All of these salts (or other similar salts) may be prepared by conventional means. All such salts are acceptable provided that they are non-toxic and do not substantially interfere with the desired pharmacological activity.

In addition, it is possible to use any salts and free base form of memantine (collectively referred to as memantine), including polymorphs, hydrates and solvates as well as amorphous forms of memantine.

In a preferred embodiment of the invention, the active ingredient is memantine hydrochloride.

In one embodiment, the memantine is formulated as a 12-hour formulation, wherein the active ingredient has at least about 70-80% dissolution after about 12 hours. The active ingredient is present in amounts ranging from about 1% w/w to about 20% w/w, preferably from about 1.6% to about 20% w/w, most preferably from about 2.5% w/w to about 20% w/w. In a preferred embodiment, the active ingredient is present in amounts of about 10 mg to about 80 mg per tablet.

In an alternate embodiment, the memantine is formulated as a 6-hour formulation, wherein the active ingredient has at least about 70-80% dissolution after about 6 hours. The active ingredient is present in an amount ranging from about 1% w/w to about 35% w/w, preferably from about 1.6% w/w to about 35% w/w, most preferably from about 5% w/w to about 35% w/w. In another preferred embodiment, the active ingredient is present in amounts of about 10 mg to about 80 mg per tablet.

To achieve the desired modified release rates, the modified release dosage form may be formulated as a polymeric coating or matrix. In one preferred embodiment, the modified release dosage form is formulated as a matrix.

Depending upon the hydrophilic (erodable or non-erodable) or hydrophobic nature of the matrix, the matrix may be a material that swells upon contact with gastric fluid to a size that is large enough to promote retention in the stomach while the subject is in the digestive state. In addition to these diffusion based matrices, the matrix may also be in an erodable form. The digestive state is induced by food ingestion and begins with a rapid and profound change in the motor pattern of the upper gastrointestinal (GI) tract. The change consists of a reduction in the amplitude of the contractions that the stomach undergoes and a reduction in the pyloric opening to a partially closed state. The result is a sieving process that allows liquids and small particles to pass through the partially open pylorus while indigestible particles that are larger than the pylorus are retropelled and retained in the stomach. In other words, biological fluids migrate through the matrix and dissolve the active ingredient which is released by diffusion through the matrix which, simultaneously, modulates the release rate. The controlled-release matrix in these embodiments of the invention is therefore selected as one that can swell to a size large enough to be retropelled and thereby retained in the stomach, causing the prolonged release of the drug to occur in the stomach rather than in the intestine. Disclosures of oral dosage forms that swell to sizes that will prolong the residence time in the stomach are found in U.S. Pat. Nos. 5,007,790, 5,582,837, and 5,972,389, as well as International (PCT) Patent Application WO 98/55107 and WO 96/26718. Each of the documents cited in this paragraph is incorporated herein by reference in its entirety.

In compositions comprising a hydrophilic matrix, the matrix is composed of an insoluble hydrophilic polymer. This polymer is chosen from cellulose esters, carboxyvinyl esters, or acrylic or methacrylic esters. On contact with biological fluids, the matrix becomes hydrated and swells, forming a network of polymers, through which polymers the soluble active principles diffuse. Furthermore, lipids, in particular glyceryl esters, can be added in order to modulate, or lessen, the matrix swelling and rate of diffusion.

However, in the present invention, lipids are not needed to modulate the diffusion of the matrix. Rather, the compositions of the claimed invention work with the normal rate of gastric diffusion, controlled in part by the thickness of the tablet. In addition, compositions with lipids may include numerous adjuvants, often expensive adjuvants, at high concentrations, which greatly increases the cost of the composition. Furthermore, such compositions are obtained by granulation and then compression of the mixture formed of the polymer, active principles and various adjuvants. These techniques often involve the use of organic solvents, which it is subsequently essential to recover in order to prevent them from dispersing into the atmosphere. In addition, traces of toxic solvents can remain in the final product, which traces necessarily have to be quantified.

In general, swellable matrices contain binders that are water-swellable polymers, and suitable polymers are those that are non-toxic, that swell in a dimensionally unrestricted manner upon imbibitions of water, and that release the drug gradually over time. Examples of polymers meeting this description include, but are not limited to the following: cellulose polymers and their derivatives including, but not limited to, hydroxymethyl cellulose, hydroxyethyl cellulose, hydroxypropyl cellulose, hydroxypropylmethyl cellulose, carboxymethylcellulose, and microcrystalline cellulose polysaccharides and their derivatives, polyalkylene oxides, polyethylene glycols, chitosan, poly(vinyl alcohol), xanthan gum, maleic anhydride copolymers, poly(vinyl pyrrolidone), starch and starch-based polymers, maltodextrins, poly (2-ethyl-2-oxazoline), poly(ethyleneimine), polyurethane hydrogels, crosslinked polyacrylic acids and their derivatives.

Further examples are copolymers of the polymers listed above, including block copolymers and graft polymers. Specific examples of copolymers are PLURONIC® and TECTONIC®, which are polyethylene oxide-polypropylene oxide block copolymers available from BASF Corporation, Chemicals Div., Wyandotte, Mich., USA. Further examples are hydrolyzed starch polyacrylonitrile graft copolymers, commonly known as "Super Slurper" and available from Illinois Corn Growers Association, Bloomington, Ill., USA.

In the compositions comprising a hydrophobic matrix, the matrix is composed of a lipid matrix agent of natural origin, for example beeswaxes, which is highly innocuous. However, its composition varies from one batch to another and its stability over time is not very satisfactory. As above, these compositions are generally obtained by granulation (wet or solvent), and then compression, involving high proportions of each of the constituents.

In the present invention, particularly preferred polymers are poly(ethylene oxide), hydroxypropyl methyl cellulose, and combinations of poly(ethylene oxide) and hydroxypropyl methyl cellulose. Most preferred is hydroxypropyl methyl cellulose. In the 12-hour modified release formulations, the polymer is present in amounts ranging from about 50% w/w to about 80% w/w, preferably from about 68% to about 77% w/w. In the 6-hour modified release formulations, the polymer is present in amounts ranging from about 20% w/w to about 70% w/w, preferably from about 54% w/w to about 65% w/w.

The prolongation in the time of maximum plasma concentration values ($T_{max}$) as compared to immediate release, is related to the in vitro dissolution release rate of the drug. The in vitro dissolution release rate of the drug depends on the composition of the matrix. By using different cellulosic matrices, in-vitro release rates (drug dissolution of more than about 70% to about 80%) can be manipulated anywhere from about 4 hours to 24 hours, preferably about 6 to about 12 hours. The formulations have a time of maximum plasma concentration (average $T_{max}$) ranging from between about 4 to about 24 hours, preferably from about 10 to about 20 hours and an in vitro release rate of more than about 70% to about 80% in about 6 to about 12 hours following entry to a use environment. Preferably, the formulations have a release rate of about 30% to about 60% in about 2 to about 6 hours. More preferably, the formulations have a release rate of about 10% to about 50% within the first hour following entry into a use environment followed by extended release; more preferably, the formulations have a release rate of about 10% to about 35% within the first hour. All of the drug from the modified release formulation does not release memantine immediately, such as not more than 80% in about 15 to about 30 minutes within the first hour following entry into a use environment. This is important so as to prevent dose dumping.

Tablets in accordance with this invention can be prepared by conventional mixing, comminution, and tabletting techniques that are well known in the pharmaceutical formulations industry. The modified release tablet, for example, may be fabricated by direct compression by punches and dies fitted to a rotary tabletting press, ejection or compression molding, granulation followed by compression, or forming a paste and extruding the paste into a mold or cutting the extrudate into short lengths. Preferably, the process used for preparing tablets is direct compression of the blend. This process is also preferred economically, because it involves fewer unit operations involving inexpensive equipment. Ordinarily, direct blending is a difficult process, and problems such as blend segregation, low compressibility and low content uniformity can occur. However, the formulations described in this invention do not exhibit any such problems.

In the present invention, one or more fillers may be used including but not limited to microcrystalline cellulose, dicalcium phosphate, lactose, derivatives of cellulose, starch, other calcium phosphates, gelatine, hydrated sugar alcohols (i.e., sorbite, mannite), polyvinyl pyrrolidone, and collidone. Preferably, fillers such as microcrystalline cellulose, dicalcium phosphate and lactose are used to modify the dissolution pattern. When hydroxypropyl methylcellulose or ethyl cellulose are used as the matrix material, the dissolution rates can be much slower than the modified release rate targeted. The slow release is because hydrophobic matrix tablets release the drug by mechanism of polymer erosion. Since the erosion from a hydrophobic matrix is very slow, the dissolution rate of the readily soluble active ingredient is also slow. Fillers are also important ingredients useful in improving the powder flow and compressibility for memantine HCl tablets.

In one embodiment, the dosage forms contain the microcrystalline cellulose as filler in amounts from about 5% w/w to about 80% w/w, more preferably from about 5% w/w to about 71% w/w, most preferably from about 7% w/w to about 40% w/w.

In another embodiment, the dosage forms contain dicalcium phosphate dihydrate as one of many fillers or as the only filler in amounts from about 5% w/w to about 80% w/w, more preferably from about 5% w/w to about 71% w/w, most preferably from about 7% w/w to about 40% w/w. In particular embodiments, the dosage forms are lactose free.

In yet another embodiment, the dosage forms contain lactose monohydrate as filler. For 12-hour release formulations, lactose monohydrate is present in amounts ranging from about 5% w/w to about 50% w/w, preferably from about 5% w/w to about 25% w/w, most preferred from about 6.9% w/w to about 15% w/w. For 6-hour release formulations, lactose monohydrate is present in amounts ranging from about 5% w/w to about 75% w/w, preferably from about 5% w/w to about 50% w/w, most preferred from about 7% w/w to about 24% w/w.

When tablets are made by direct compression, the addition of lubricants may be helpful and is sometimes important to promote powder flow and to prevent or lessen "capping" (the breaking off of a portion of the tablet) when the pressure is relieved. Useful lubricants include magnesium stearate, and hydrogenated vegetable oil (preferably hydrogenated and refined triglycerides of stearic and palmitic acids). In a preferred embodiment, the lubricant is magnesium stearate. For the 12-hour release formulations, the magnesium stearate is present in amounts ranging from about 0.8% w/w to about 1.2% w/w, preferably from about 0.9% w/w to about 1.1% w/w. For the 6-hour release formulations, the magnesium stearate is present in amounts ranging from about 0.4% w/w to about 0.6% w/w, preferably about 0.5% w/w. Additional excipients may be added to enhance tablet hardness, powder flowability, and tablet friability and to reduce adherence to the die wall.

In accordance with the present invention, a modified release pharmaceutical composition is provided for the once daily administration of memantine or a pharmaceutically acceptable salt thereof, preferably its HCl salt, to a human or animal subject. The memantine formulations of the invention are suitable for the treatment of CNS diseases, including but not limited to the treatment of Alzheimer's disease, Parkinson's disease, AIDS dementia (U.S. Pat. No. 5,506,231, see also Parsons et al., Neuropharmacology 1999 June; 38(6):735-67), neuropathic pain (U.S. Pat. No. 5,334,618), cerebral ischemia (U.S. Pat. No. 5,061,703), epilepsy, glaucoma, hepatic encephalopathy, multiple sclerosis, stroke, depression (U.S. Pat. No. 6,479,553), tardive dyskinesia, malaria, Borna virus, Hepatitis C (U.S. Pat. Nos. 6,034,134 and 6,071,966). Additional pathologies for treatment of which memantine is suitable are disclosed in U.S. Pat. Nos. 5,614,560 and 6,444,702. Of particular interest is the ability to provide uninterrupted pain relief. Accordingly, the present invention further provides a method for the therapeutic or prophylactic treatment of CNS disorders in a human or animal subject, the method including administering to the subject, a composition in accordance with the present invention.

For purposes of the present invention, "sustained release or modified release" means that the release of the therapeutically active agent occurs over an extended period of time leading to lower peak plasma concentrations ($C_{max}$) and a prolonged $T_{max}$ as compared to "immediate release." The "dissolution requirements" and "disintegration requirements" referred to above are conducted using the equipment and tests specified in the USP XXIV and conducted pursuant to the individual Official Monographs of USP XXIV (U.S. Pharmacopoeia and National Formulary, USP XXIV/NF 19, Chapter 1088, pages 2051-2056, 2000), incorporated herein by reference, for the particular therapeutically active agent(s) included in the tablet core.

A "therapeutically effective amount" means the amount of a compound that, when administered to a mammal for treating a state, disorder or condition is sufficient to effect such treatment. The "therapeutically effective amount" will vary depending on the compound, the disease and its severity and the age, weight, physical condition and responsiveness of the mammal to be treated. According to the instant invention, in one embodiment, a therapeutically effective amount of memantine is an amount effective to treat CNS disorders, including Alzheimer's disease or Parkinson's disease. In another embodiment, a therapeutically effective amount is an amount effective to treat neuropathic pain, or other painful conditions such as visceral hypersensitivity. Other uses include, but are not limited to, the treatment of dementia and depression. The effective amount of the drug for pharmacological action, and therefore the tablet strength, depends on the disease itself, e.g., in Alzheimer's disease, the patient is initially given a 5 mg dose and the dosage is progressively increased to 10 mg twice a day. Additional doses evaluated in clinical trials include 40 mg/day.

The term "pharmaceutically acceptable" means biologically or pharmacologically compatible for in vivo use in animals or humans, and preferably means approved by a regulatory agency of the Federal or a state government or listed in the U.S. Pharmacopeia or other generally recognized pharmacopeia for use in animals, and more particularly in humans.

As used herein, the term "treat" is used herein to mean to relieve or alleviate at least one symptom of a disease in a subject, including for example, pain, Alzheimer's disease, vascular dementia, or Parkinson's disease. The term "treat" may mean to relieve or alleviate the intensity and/or duration of a manifestation of disease experienced by a subject in response to a given stimulus (e.g., pressure, tissue injury, cold temperature, etc.). For example, in relation to dementia, the term "treat" may mean to relieve or alleviate cognitive impairment (such as impairment of memory and/or orientation) or impairment of global functioning (activities of daily living, ADL) and/or slow down or reverse the progressive deterioration in ADL or cognitive impairment. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject. Within the meaning of the present invention, the dementia is associated with a CNS disorder, including without limitation neurodegenerative diseases such as Alzheimer's disease (AD), Down's Syndrome and cerebrovascular dementia (VaD).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%. Alternatively, particularly with respect to biological systems or processes, the term can mean within an order of magnitude, preferably within 5-fold, and more preferably within 2-fold, of a value. Where particular values are described in the application and claims, unless otherwise stated the term "about" means within an acceptable error range for the particular value. For example, when referring to a period of time, e.g., hours, the present values (±20%) are more applicable. Thus, 6 hours can be, e.g., 4.8 hours, 5.5 hours, 6.5 hours, 7.2 hours, as well as the usual 6 hours.

The term "similarity factor" or "f2 factor" as used herein refers to one way of comparing dissolution profiles of two different products. (Multisource Pharmaceutical Products: Guidelines on Registration Requirements to establish Interchangeability, Quality Assurance and Safety: Medicines, Essential Drugs and Medicines Policy, World Health Organization, 1211 Geneva 27, Switzerland, pages 11-12, 2004, incorporated herein by reference). This model-independent mathematical approach compares the dissolution profile of the two products: test and reference (or two strengths, or pre- and post-approved products from the same manufacturer). Tests are recommended to be performed under the same test conditions. The dissolution time points for both the profiles should be the same, for example for immediate release products e.g. 10, 15, 30, 45, 60 minutes and for extended release products, e.g., 1, 2, 3, 5 and 8 hours. Only one time point should be considered after 85% dissolution of the reference product. An f2 value of 50 or greater (50-100) ensures sameness or equivalence of the two curves, and thus the performance of the two products. The similarity factor f2 should be computed using the equation:

$$f_2 = 50 \log \{[1+(1/n)\sum_{t=1}^{n}(R_t-T_t)^2]^{-0.5} 100\}$$

where Rt and Tt are the cumulative percentage of the drug dissolved at each of the selected n time points of the comparison (reference) and (test) product respectively. For products which are very rapidly dissolving, i.e. more than 85% dissolution in 15 minutes or less, a profile comparison is not necessary. For extended release beaded capsules, where the strength differs only in the number of beads containing active moiety, dissolution profile comparison (f2>50) under one recommended test condition is sufficient for biowaivers. A biowaiver is a waiver by regulatory authority of a requirement for bioequivalence of a new formulation compared to a previous one. Whereas for extended release tablets, as in the present invention, when the drug product is in the same dosage form but in a different strength, and is proportionally similar in its active and inactive ingredients and has the same drug release mechanism, a lower strength can be granted a biowaiver if it exhibits similar dissolution profiles, f2>50, in three diverse pH buffers (between pH 1.2 and 7.5) by the recommended test method.

The term "dissolution stability" as used herein refers to the similarity of dissolution profiles (similarity factor greater than 50, in comparison to initial) obtained at different periods of storage at varying temperature and humidity conditions.

The term "substantially the same dissolution stability" means similarity factor f2 of greater than 50 as compared to a reference dissolution profile.

The term "entry into a use environment" means contact of a formulation of the invention with the gastric fluids of the patient to whom it is administered, or with a fluid intended to simulate gastric fluid.

EXAMPLES

The present invention will be better understood by reference to the following Examples, which are provided as exemplary of the invention, and not by way of limitation.

Example 1

Preparation of Memantine HCl Modified Release Tablets

The present example describes the process of developing memantine hydrochloride modified release tablets in 7, 10, 20, 28, 40 mg and 80 mg dosages.

The following tables provide the exemplary makeup of modified release tablets including the active components, polymeric matrix, and other excipients for the specified dosage forms with specific the target release time periods.

TABLE 1

|  | mg per tablet | | | | % w/w | | | |
| --- | --- | --- | --- | --- | --- | --- | --- | --- |
|  | 10 mg | 20 mg | 40 mg | 80 mg | 10 mg | 20 mg | 40 mg | 80 mg |
| 12 Hour Formulation STRENGTH: | | | | | | | | |
| Memantine Hydrochloride | 10 | 20 | 40 | 80 | 2.5% | 5.0% | 10.0% | 18.1% |
| HPMC (Synchron KF) | 306 | 306 | 306 | 306 | 76.5% | 76.5% | 76.5% | 69.6% |
| Lactose | 60 | 50 | 30 | 30 | 15.0% | 12.5% | 7.5% | 6.9% |
| Fumed Silica (Cab-O-Sil) | 4 | 4 | 4 | 4 | 1.0% | 1.0% | 1.0% | 0.9% |

TABLE 1-continued

|  | mg per tablet | | | | % w/w | | | |
| --- | --- | --- | --- | --- | --- | --- | --- | --- |
|  | 10 mg | 20 mg | 40 mg | 80 mg | 10 mg | 20 mg | 40 mg | 80 mg |
| Talc | 16 | 16 | 16 | 16 | 4.0% | 4.0% | 4.0% | 3.6% |
| Magnesium Stearate | 4 | 4 | 4 | 4 | 1.0% | 1.0% | 1.0% | 0.9% |
| Total | 400 | 400 | 400 | 440 | 100.0% | 100% | 100.0% | 100.0% |
| 6 Hour Formulation STRENGTH: | | | | | | | | |
| Memantine Hydrochloride | 10 | 20 | 40 | 80 | 5.0% | 10.0% | 20.0% | 33.3% |
| HPMC (Synchron KF) | 130 | 130 | 130 | 130 | 65.0% | 65.0% | 65.0% | 54.2% |
| Lactose | 48 | 38 | 18 | 18 | 24.0% | 19.0% | 9.0% | 7.5% |
| Fumed Silica (Cab-O-Sil) | 2 | 2 | 2 | 2 | 1.0% | 1.0% | 1.0% | 0.8% |
| Talc | 9 | 9 | 9 | 9 | 4.5% | 4.5% | 4.5% | 3.8% |
| Magnesium Stearate | 1 | 1 | 1 | 1 | 0.5% | 0.5% | 0.5% | 0.4% |
| Total | 200 | 200 | 200 | 240 | 100.0% | 100.0% | 100.0% | 100.0% |

The following tables illustrate the composition of modified release tablets including the active components, polymeric matrix, and microcrystalline cellulose and/or dicalcium phosphate fillers.

TABLE 2

| 6 Hour Formulation | mg per tablet | | | | % w/w | | | |
| --- | --- | --- | --- | --- | --- | --- | --- | --- |
| STRENGTH: | 7 mg | 28 mg | 7 mg | 28 mg | 7 mg | 28 mg | 7 mg | 28 mg |
| Memantine Hydrochloride | 7 | 28 | 7 | 28 | 3.2 | 12.7 | 3.2 | 12.7 |
| HPMC (Synchron KF) | 130 | 130 | 130 | 130 | 59.1 | 59.1 | 59.1 | 59.1 |
| Microcrystalline Cellulose | 71 | 50 | 0 | 0 | 32.3 | 22.7 | 0.0 | 0.0 |
| Dicalcium Phosphate | 0 | 0 | 71 | 50 | 0.0 | 0.0 | 32.3 | 22.7 |
| Fumed Silica (Cab-O-Sil) | 2 | 2 | 2 | 2 | 0.9 | 0.9 | 0.9 | 0.9 |
| Talc | 9 | 9 | 9 | 9 | 4.1 | 4.1 | 4.1 | 4.1 |
| Magnesium Stearate | 1 | 1 | 1 | 1 | 0.5 | 0.5 | 0.5 | 0.5 |
| Total | 220 | 220 | 220 | 220 | 100.0 | 100.0 | 100.0 | 100.0 |

Test batches of each of the tablets were prepared according to the process outlined below.

Preparation of Blend for Tabletting. The memantine HCl, HPMC (hydroxypropyl methyl cellulose, Synchron oral carrier vehicle, type KF), lactose monohydrate, NF and colloidal silicon dioxide, NF, (Cab-O-Sil®) are mixed in a V-Blender for 10 minutes. Talc (an anti-adherant component) is added to the above mixture and mixed for 5 minutes. Finally, magnesium stearate is added to the mixture and mixed for 5 minutes. The blend is discharged in a container lined with double polyethylene bag liners and labeled as "Final Blend for Compression".

Compression of Tablets.

The blend is compressed using a rotary tablet press. The tablet shape for 12 hrs dissolution tablets is circular and the target average tablet weight is about 400 mg. The diameter of the tablets is 0.4375 inch. The tablet shape for 6 hrs dissolution tablets is circular and the target average tablet weight is about 200 mg. The diameter of the tablets is 0.3125 inch.

During compression, the following controls are performed periodically: tablet weight, tablet hardness, and tablet thickness. In addition, dissolution tests were conducted on the 10 mg, 20 mg, and 40 mg tablets for the 6 hour release formulations, as well as the 20 mg for the 12 hour release formulation. For dissolution tests, tablets of different hardness were tested using USP Apparatus II using 900 ml of pH 1.2 buffer. (U.S. Pharmacopoeia and National Formulary, USP XXIV/NF 19, Chapter 711, pages 1941-1943, 2000). The data are presented in Table 3 below.

TABLE 3

|  | 6 hr release | | | 12 hr release |
| --- | --- | --- | --- | --- |
|  | 10 mg | 20 mg | 40 mg | 20 mg |
|  | Hardness | | | |
| Time (hrs) | 7.2-8.5 kp | 7.3-8.4 kp | 7.2-8.3 kp | 7.8-11.0 kp |
| 0 | 0 | 0 | 0 | 0 |
| 1 | 32 | 32 | 28 | 19 |
| 2.5 | 54 | 52 | 49 | 35 |
| 4 | 69 | 68 | 64 | 47 |
| 6 | 83 | 81 | 78 | 58 |
| 8 | 91 | 91 | 89 | 67 |
| 12 | 98 | 98 | 99 | 81 |

Figure 2:
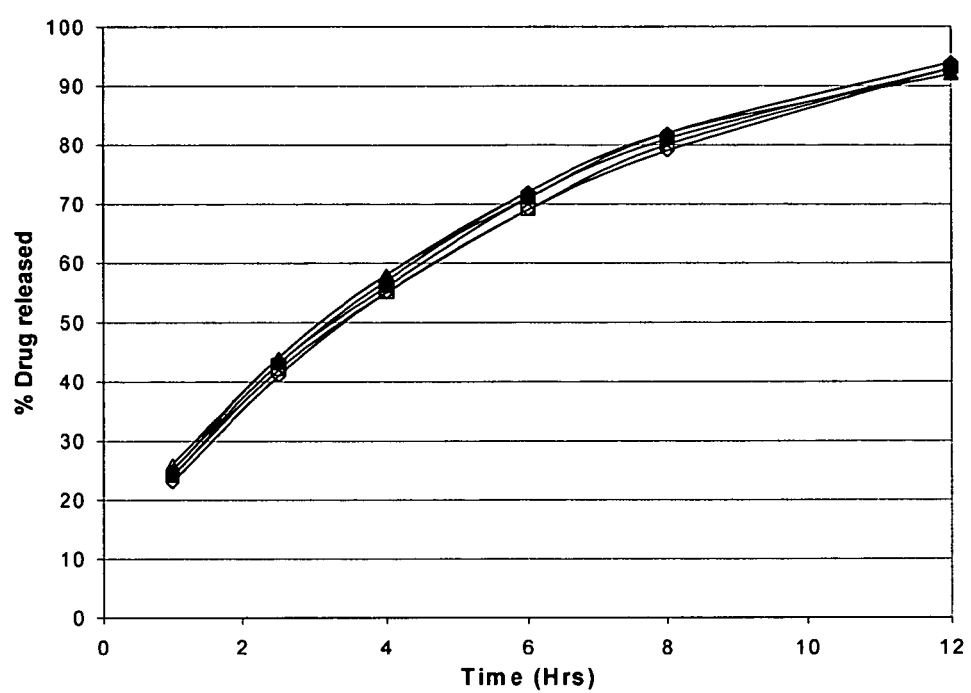
FIG. 2 shows the dissolution rates for the scaled up batches of 10, 20, and 40 mg memantine HCl tablets after six months of storage conditions at 40° C./75% RH. Dissolution is shown as percent drug released over time (hours). The open diamond represents the 40 mg strength; the open square represents the 20 mg strength; and the open triangle represents the 10 mg strength. These open shapes represent measurements at 6 months. The corresponding filled shapes represent the baseline measurements.
Figure 3:
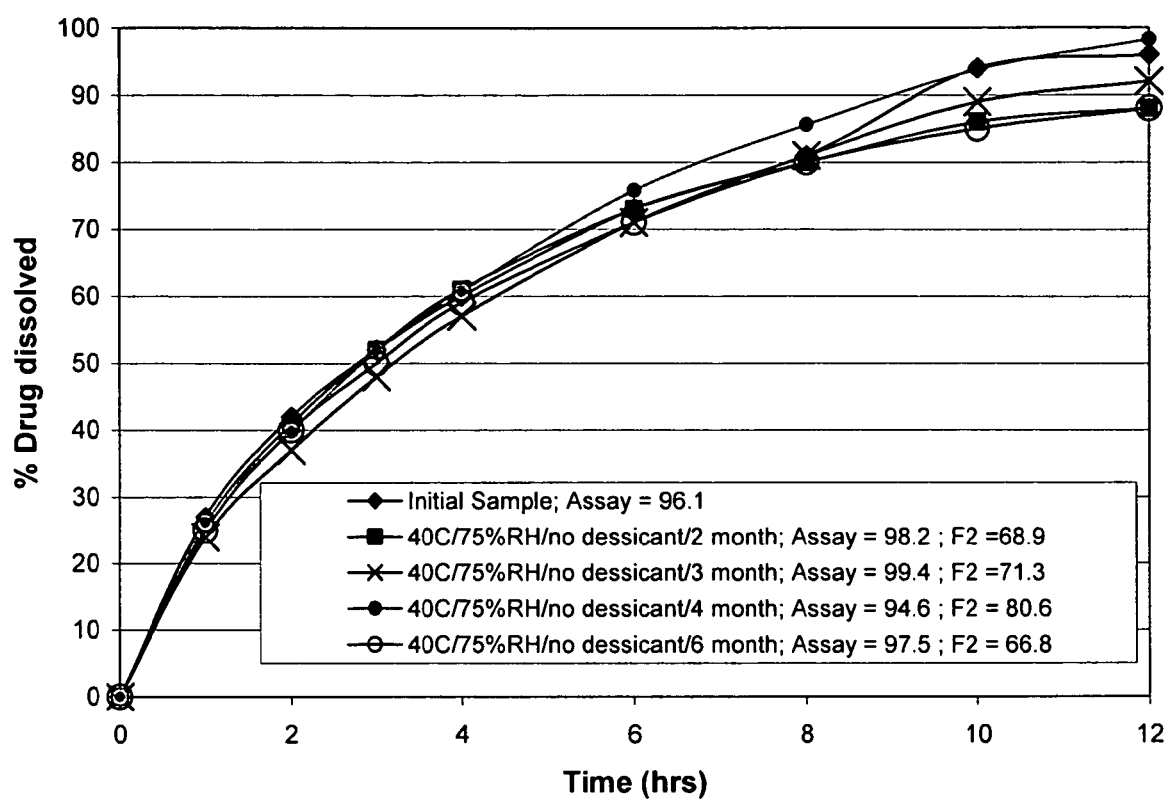
FIG. 3 shows the stability of dissolution profiles for a 6 hour release formulation up to 6 months at 40° C./75% RH. The dissolution profiles show the percentage of drug dissolved for various batches over time (hours). The age of each sample is indicated in FIG. 3.
Figure 4:
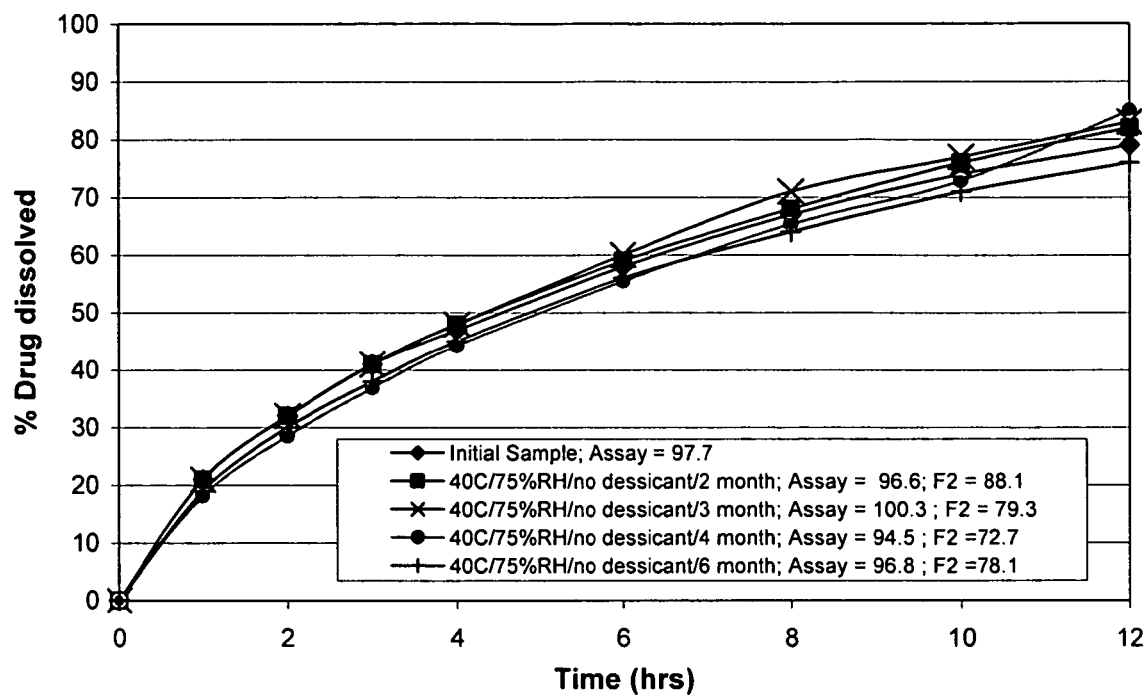
FIG. 4 shows the stability of dissolution profiles for a 12 hour release formulation up to 6 months at 40° C./75% RH. The dissolution profiles show the percentage of drug dissolved for various batches over time (hours). The age of each sample is indicated in FIG. 4.
Figure 10:
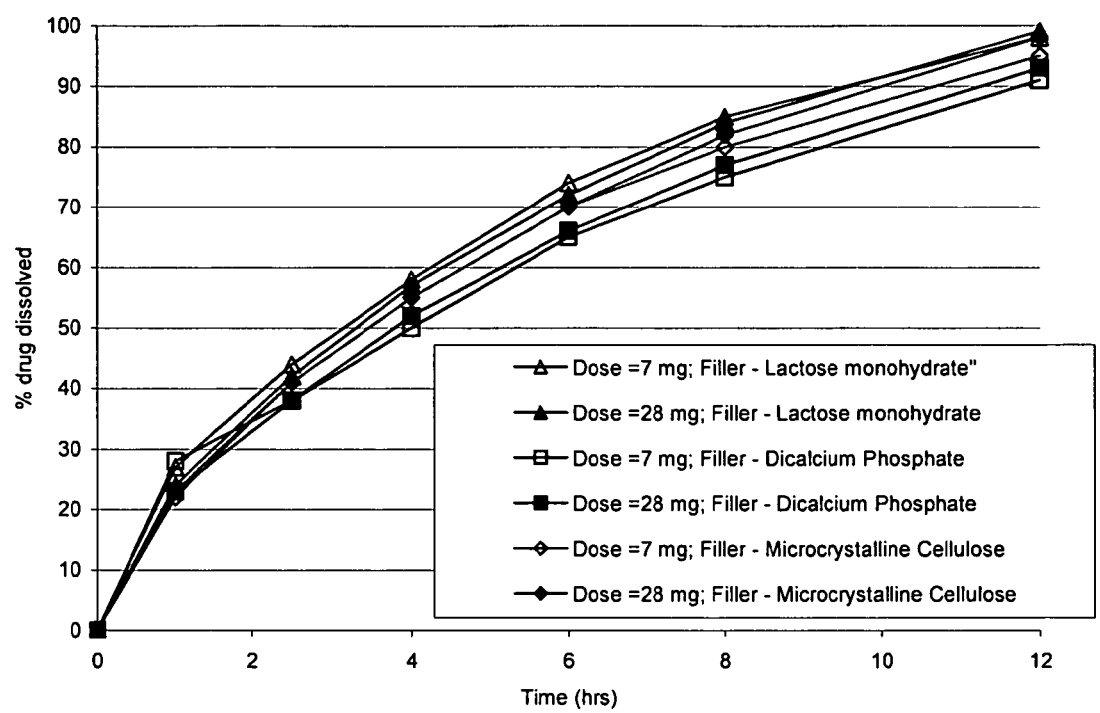
FIG. 10 shows the dissolution profiles of modified release memantine tablets prepared for doses 7 mg and 28 mg using three different fillers—lactose monohydrate, dicalcium phosphate and microcrystalline cellulose. The data show that each work about the same dissolution. The shape of the data points for each composition is indicated in FIG. 10.

The formulations for the Memantine HCl tablets for strengths 10, 20 and 40 mg were scaled up. These batches showed excellent stability after storage at 40 C/75% RH in HDPE bottles without desiccant after two months and six months. See FIGS. 1 and 2 for dissolution results, wherein all tablets performed satisfactorily, at or close to the baseline value. In addition, 20 mg tablets were tested for stability of dissolution of the 6 hour and 12 hour release formulations. Dissolution profiles for the batches (01074H 6 hour and 01075H 12 hour) up to 6 months at 40 C/75% RH are shown in FIGS. 3 and 4. The dissolution profiles of modified release memantine tablets prepared for doses 7 mg and 28 mg using three different fillers—lactose monohydrate, dicalcium phosphate and microcrystalline cellulose are provided in FIG. 10.

Example 2

Pharmacokinetic Study of Memantine

The present example demonstrates the bioavailability of immediate release memantine tablets as compared to modified release memantine tablets.

Materials and Methods

The study design in the present example was a 57-day single-center, open-label study in 24 young healthy subjects, ages ranging from 18 to 35 years old. Subjects underwent a screening evaluation consisting of a complete medical history, complete physical examination with vital signs, 12-lead ECG, clinical laboratory evaluations, consisting of a CBC (including differential), clinical chemistry, urinalysis, RPR/VDRL, Anti HIV 1 and 2 tests, drugs of abuse screen (including alcohol and nicotine), Anti-HCV and HbsAg. Female subjects had a β-hCG serum pregnancy test performed at screening and a urine pregnancy test on Day −1.

Inclusion criteria included informed consent, normal physical examination, healthy adults between 18 and 35 years of age, non-smokers, within 15% of ideal body weight in relation to height, and a sitting pulse rate of not less than 50 beats per minute by palpitation, and a heart rate of not less than 50 beats per minute as recorded by ECG. Exclusion criteria included hypersensitivity to memantine or other NMDA antagonists, presence of any clinically significant disease, sitting systolic blood pressure greater than 180 mmHg or less than 100 mmHg or a sitting diastolic blood pressure greater than 100 mmHg or less than 60 mmHg at screening, significant ECG abnormalities, history of alcohol or substance abuse, positive tests to drugs of abuse, consumption of caffeine within 48 hours or alcohol within 72 hours prior to testing, participation in other clinical investigation within 30 days of study, clinical conditions associated with memantine, concomitant medications, or females breastfeeding.

There were three treatment regimens including an immediate release memantine HCl 10 mg tablet (30 minutes dissolution, Treatment A), a modified release memantine HCl 20 mg tablet (formulation I, 6 hour dissolution, Treatment B), and a second modified release memantine HCl 20 mg tablet (formulation II, 12 hour dissolution, Treatment C). The subjects received three treatments on study days 1, 22, and 43 in a crossover manner separated by a 21-day washout period based on randomized treatment sequences. The immediate release treatment was administered twice a day, at 0800 and 1200 hours, for one day. The modified release treatments were administered once a day at 0800 hours. Formulation A is discussed in detail in co-pending application filed simultaneously with the present application.

Subjects were admitted into a non-smoking environment at approximately 1900 hours on Days −1, 21, and 42. There were a total of six overnight stays for each subject (Days −1, 1, 21, 22, 42 and 43). Subjects were subjected to diet and fluid control and received no concomitant medications.

Vital signs and adverse events were recorded over the course of the study. Blood samples for the determination of memantine were obtained from each subject during the course of the study 1, 22, and 43 on study day after the 0800 hour drug administration at the following times: 0.0 hour (pre-dose), every hour for the first 12 hours, 14, 24, 36, 48, 72, 96, 144, 192, 240, 288 and 336 hours post dose. A number of blood samples were subjected to pharmacokinetic analysis for the determination of memantine concentration.

Approximately 5 mL of blood were collected per sample following dosing on Days 1, 22, and 43. Blood samples were centrifuged and the plasma for each sample was harvested. The samples were then flash frozen in an isopropyl alcohol/dry ice bath and stored in a −70° C. freezer.

Bioanalytical Procedures.

The bioanalytical procedure used to measure the plasma memantine concentrations was validated to demonstrate accuracy, linearity, reproducibility, and precision of the analytical procedures. An LC/MS/MS (liquid chromatography/mass spec/tandem mass spec) method was developed for the determination of memantine in human plasma. After the addition of 10 ng of [$^2$H$_6$] memantine internal standard and 0.5 M sodium carbonate buffer to plasma standards and samples, the compounds were extracted with ethyl acetate. The organic layer was isolated and dried at room temperature under the vacuum in a sample concentrator (Savant). The dry residue was analyzed after reconstitution in mobile phase. The components of the reconstituted samples were separated on a Zorbax SB-C8 column (150×4.6 mm, 3.5 μm) and detected by atmospheric pressure chemical ionization (APCI) with a selected reaction monitoring (SRM) positive ion mode. The SRM used precursor→positive product ions of m/z 180→163 and m/z 186→169 to monitor memantine and its internal standard, respectively. The protonated molecular ions of memantine and [$^2$H$_6$] memantine are the precursor ions for the SRM mode. The peak height ratio of memantine product ion to that of its internal standard was the response used for quantification. The plasma standards of the method validation showed accuracy within ±8.2% deviation and precision did not exceed 7.6% CV. Accuracy for the determination of memantine in plasma quality controls was within ±8.8% deviation with a precision not exceeding 9.8% CV. The lower limit of quantification of the method was 0.5 ng/mL.

Pharmacokinetic Analysis.

Pharmacokinetic parameters were estimated using Win-Nonlin (version 3.3, Pharsight Corporation, Mountain View, Calif.). The following parameters were determined from the plasma concentrations of memantine following single dose administration: the area under the plasma concentration time curve ($AUC_{0-t}$, $AUC_{0-24}$, and $AUC_{0-\infty}$), maximum plasma concentration ($C_{max}$), time of maximum plasma concentration ($T_{max}$), elimination half-life ($T_{1/2}$) and mean residence time (MRT). Maximum plasma concentrations ($C_{max}$) and the time of the maximum concentration ($T_{max}$) for memantine were determined by observation.

The first-order rate constant, $\lambda_z$, describing the terminal decline in plasma was estimated by WinNonlin (version 3.3) using log-linear regression of the terminal linear phase of the mean plasma concentration-time curves of memantine.

Estimates of terminal elimination half-life ($T_{1/2}$) in hours were calculated with equation 1:

$$T_{1/2} = \frac{0.693}{\lambda_z}. \qquad \text{Eq. 1}$$

The area under the plasma concentration versus time curve up to the last measurable concentration at time t ($AUC_{0-t}$) or at 24 hours ($AUC_{0-24}$) was estimated by numerical integration using the linear trapezoidal rule (Equation 2).

$$AUC_{0-t} = \sum_{i=2}^{n} 0.5 \cdot (C_i + C_{i-1}) \cdot (t_i - t_{i-1}) \quad \text{Eq. 2}$$

where $C_i$ was the plasma concentration at the corresponding sampling time point $t_i$.

Area under the plasma concentration-time curve up to time infinity ($AUC_{0-\infty}$) of memantine was computed using the following (Equation 3):

$$AUC_{0-\infty} = AUC_{0-t} + \frac{C_{last}}{\lambda_z} \quad \text{Eq. 3}$$

where $C_{last}$ is the last measurable concentration in the concentration-time profile.

MRT was calculated using the following (Equation 4):

$$MRT = \frac{AUMC}{AUC_{0-\infty}} \quad \text{Eq. 4}$$

where AUMC is the area under the first moment curve.

Descriptive statistics for the memantine pharmacokinetic parameters $C_{max}$, $t_{max}$, $AUC_{0-t}$, $AUC_{0-24}$, $AUC_{0-\infty}$, $t_{1/2}$, and MRT were provided for subjects who completed the study. Between-treatment comparisons were made using ANOVA appropriate for a 3-way crossover design.

Results

Adverse Events.

There were no serious adverse events reported. Nineteen (82.6%) of the twenty-three subjects reported a total of 42 treatment emergent adverse events following administration of Treatments A, B, and C. There were no significant differences in the number of adverse events observed with any treatment. A total of 14, 12, and 16 adverse events were observed following Treatments A, B, and C, respectively. The most common adverse events (i.e., occurring in 3 or more subjects) were headache, dizziness, flatulence, and infection.

Pharmacokinetic Results.

Figure 5:
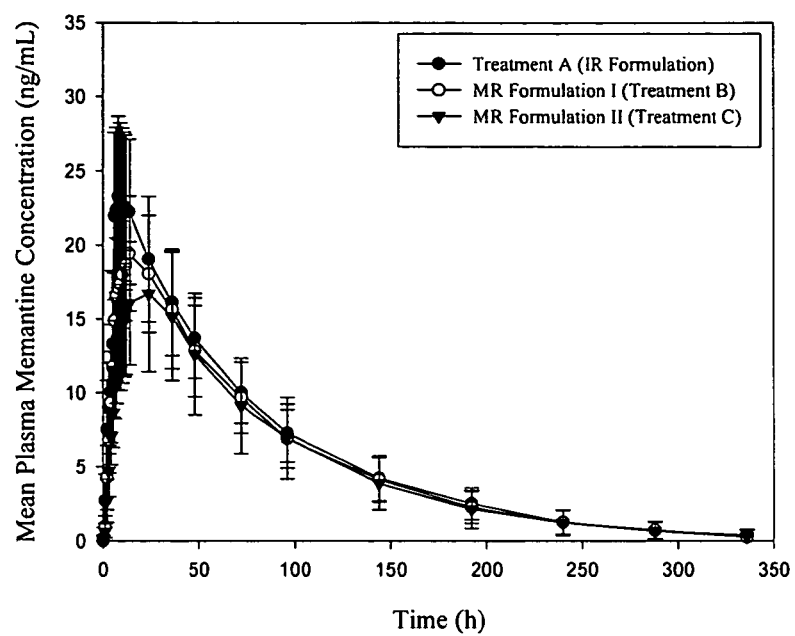
FIG. 5 depicts the mean plasma concentrations of memantine following administration of 20 mg modified release tablets in comparison to two 10 mg immediate release tablets administered four hour apart in young healthy male and female subjects over time (hours). Treatment A (closed circle) represents the immediate release formulation. Treatment B (open circle) represents a modified release formulation. Treatment C (inverted triangle) also represents a modified release formulation.
Figure 6:
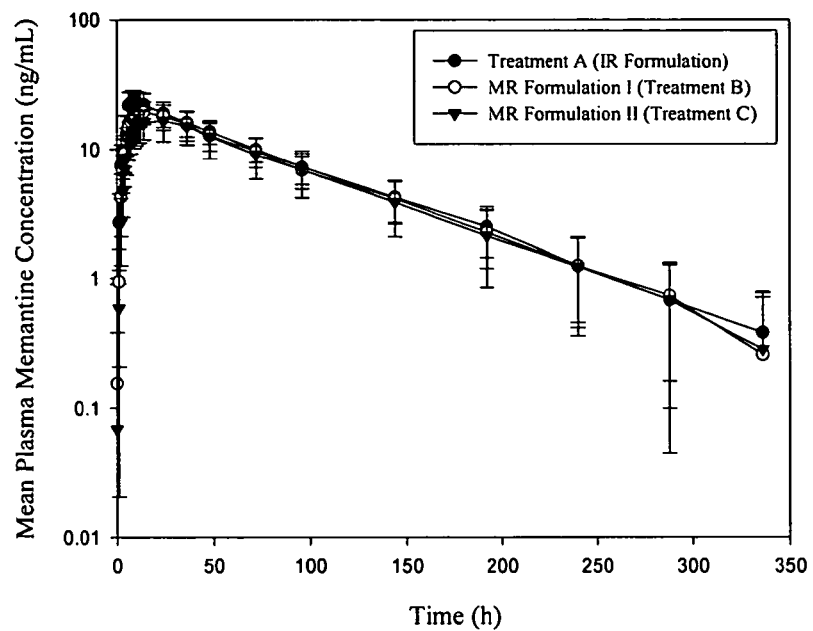
FIG. 6 depicts the mean plasma concentrations of memantine following administration of 20 mg modified release tablets of the present invention and two 10 mg immediate release tablets administered four hours apart in young healthy male and female subjects on a semi-log scale. Treatment A (closed circle) represents the immediate release formulation. Treatment B (open circle) represents a modified release formulation. Treatment C (inverted triangle) also represents a modified release formulation.
Figure 7:
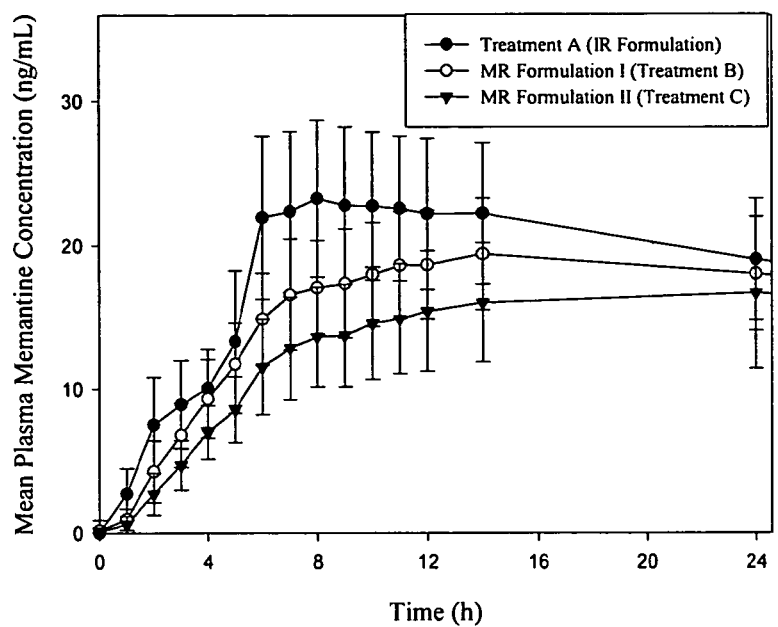
FIG. 7 depicts a truncated 24-hour profile of mean plasma concentrations of memantine following administration of memantine 20 mg modified release tablets of the present invention in comparison to two 10 mg immediate release formulation tablets administered four hours apart in young healthy male and female subjects. Treatment A (closed circle) represents the immediate release formulation. Treatment B (open circle) represents a modified release formulation. Treatment C (inverted triangle) also represents a modified release formulation.

The mean plasma concentrations of memantine are illustrated in FIG. 5 (linear scale) and in FIG. 6 (semi-log scale). FIG. 7 presents mean plasma concentrations of memantine during the first 24 hours post-dose. Peak memantine concentration was highest following administration of the IR formulation (Treatment A) and lowest following administration of the MR formulation H (Treatment C).

The mean (±SD) pharmacokinetic parameters of memantine following Treatments A, B and C are listed below.

TABLE 4

| Parameter | Treatment A IR Formulation I (n = 20) | Treatment B MR Formulation I (n = 20) | Treatment C MR Formulation II (n = 20) |
| --- | --- | --- | --- |
| $C_{max}$ (ng/mL) | 24.92 ± 4.82 | 20.37 ± 3.83 | 17.48 ± 4.60 |
| $T_{max}$ (h) | 8.2 ± 2.0 | 12.1 ± 2.1 | 19.3 ± 7.3 |
| $AUC_{0-24}$ (ng · h/mL) | 435.7 ± 87.0 | 367.2 ± 66.8 | 303.3 ± 78.2 |
| $AUC_{0-t}$ (ng · h/mL) | 1898.2 ± 453.0 | 1755.7 ± 468.9 | 1653.8 ± 589.8 |
| $AUC_{0-\infty}$ (ng · h/mL) | 1969.0 ± 455.8 | 1828.0 ± 489.9 | 1730.1 ± 609.4 |
| $T_{1/2}$ (h) | 57.4 ± 14.2 | 59.6 ± 15.4 | 59.1 ± 15.5 |
| MRT (h) | 83.9 ± 17.8 | 87.4 ± 19.4 | 89.0 ± 20.2 |

Statistical comparisons of memantine parameters are presented below in Table 5.

TABLE 5

| | Treatment B vs. Treatment A | | Treatment C vs. Treatment A | |
| --- | --- | --- | --- | --- |
| Parameter | Least-Squares Means Ratio | 90% Confidence Interval | Least-Squares Means Ratio | 90% Confidence Interval |
| $C_{max}$ | 81 | 76.65-85.75 | 70 | 65.93-73.77 |
| $AUC_{0-24}$ | 84 | 80.23-87.79 | 69 | 66.00-72.22 |
| $AUC_{0-t}$ | 91 | 83.90-99.10 | 84 | 77.15-91.14 |
| $AUC_{0-\infty}$ | 92 | 84.29-99.04 | 85 | 78.06-91.73 |

Absorption of memantine from the modified release tablets was delayed as compared to the immediate release tablet. The rate and extent of absorption of memantine were reduced following administration of the modified release formulations as compared to the immediate release formulation. Importantly, the rate of absorption ($T_{max}$) was delayed from 8.2 hours for the IR tablet (i.e., about 4 hours after the administration of the second tablet) to 12.1 hours and 19.3 for the two MR formulations. While the moderate release had slower rate and extent of absorption, there was better tolerability of the moderate release dose. No differences were observed in the terminal elimination half-life between treatments.

The 90% confidence intervals for the comparison of the log-transformed $C_{max}$, $AUC_{0-24}$, $AUC_{0-t}$ and $AUC_{0-\infty}$ for Treatment B (MR Formulation I) versus Treatment A (IR tablet) showed a significant reduction in mean $C_{max}$ value of the MR Formulation I but not in the AUC parameter values as compared to the IR tablet. The 90% confidence intervals for the comparison of the log-transformed $C_{max}$, $AUC_{0-24}$, $AUC_{0-t}$ and $AUC_{0-\infty}$ for Treatment C (MR Formulation II) versus Treatment A (IR tablet) showed significant reductions in mean $C_{max}$ and AUC values of MR Formulation II as compared to the IR tablet.

Discussion

In this study, single daily doses of 20 mg memantine, administered as two 10 mg doses of an immediate release tablet, separated by a 4-hour interval, were found to be safe and well-tolerated. There were no serious adverse events observed in this study.

The rate and extent of absorption of memantine was highest following administration of the immediate release tablets. $C_{max}$ values averaged 24.92, 20.37 and 17.48 ng/mL for the immediate release tablet (Treatment A), the modified release tablet formulation I (Treatment B) and the modified release tablet formulation II (Treatment C), respectively. $AUC_{0-\infty}$ averaged 1969, 1827 and 1730 ng·h/mL for the immediate release tablet (Treatment A), the modified release tablet formulation I (Treatment B) and the modified release tablet formulation II (Treatment C), respectively. Mean $T_{max}$ was 8.2 hours, 12.1 hours and 19.3 hours, for Treatments A, B and C, respectively.

The 90% confidence intervals for the comparison of the log-transformed $C_{max}$, $AUC_{0-24}$, $AUC_{0-t}$ and $AUC_{0-\infty}$ for Treatment B (MR Formulation I) versus Treatment A (IR tablet) showed a significant reduction in mean $C_{max}$ value of MR Formulation I but not in the AUC parameter values relative to the IR tablet. The 90% confidence intervals for the comparison of the log-transformed $C_{max}$, $AUC_{0-24}$, $AUC_{0-t}$ and $AUC_{0-\infty}$ for Treatment C (MR Formulation II) versus Treatment A (IR tablet) showed significant reductions in mean $C_{max}$ and AUC values of MR Formulation II relative to the IR tablet.

No differences were observed in the terminal elimination half-life of memantine across the different treatments. There were no statistically significant differences in mean elimination half-life or mean weight-adjusted $C_{max}$, $AUC_{0-t}$, and $AUC_{0-\infty}$ values between male and female subjects following administration of the IR or MR formulations.

In conclusion, the delayed $T_{max}$ for the two modified-release formulations is indicative of the slower absorption rate compared to the immediate-release tablets and demonstrates that the desired release characteristics were obtained. Both formulations delayed $T_{max}$ and are therefore acceptable. Treatment B (6 Hour formulation) had greater bioavailability than Treatment C (12 hour formulation).

Example 3

Dissolution Rates of Dose-Proportional Modified Release Memantine

The present example demonstrates the different dissolution rates for dose proportional 6 hour release formulations of 10 mg, 20 mg, and 40 mg memantine hydrochloride.

The following table provides the makeup of modified release tablets including the active components, polymeric matrix, and other excipients for the specified dosage forms with specific the target release time periods.

TABLE 6

| Batch # | REF PK Batch | A | B | C |
|---|---|---|---|---|
| Memantine HCl | 20 | 10 | 20 | 40 |
| Syncrhon KF | 130 | 65 | 130 | 260 |
| Lactose Monohydrate | 38 | 19 | 38 | 76 |
| Cab-O-Sil ® | 2 | 1 | 2 | 4 |
| Talc | 9 | 4.5 | 9 | 18 |
| Mg Stearate | 1 | 0.5 | 1 | 2 |
| Total | 200 | 100 | 200 | 400 |
| Tooling Dimension | 0.3125 | 0.2500 | 0.2500 × 0.5918 | 0.4900 × 0.7500 |
| Tablet Thickness (in) | 0.1689 | 0.1371 | 0.1227 | 0.1280 |
| Tablet Shape | Circular | Circular | Oval | Oval |
| Calculated Area/Vol (inch$^{-1}$) | | 31.56 | 31.56 | 31.56 |
| Maximum Hardness Obtained | 17.6 | 11.7 | 10.0 | 6.7 |

Dissolution of Dose Proportional Formulation.

Figure 8:
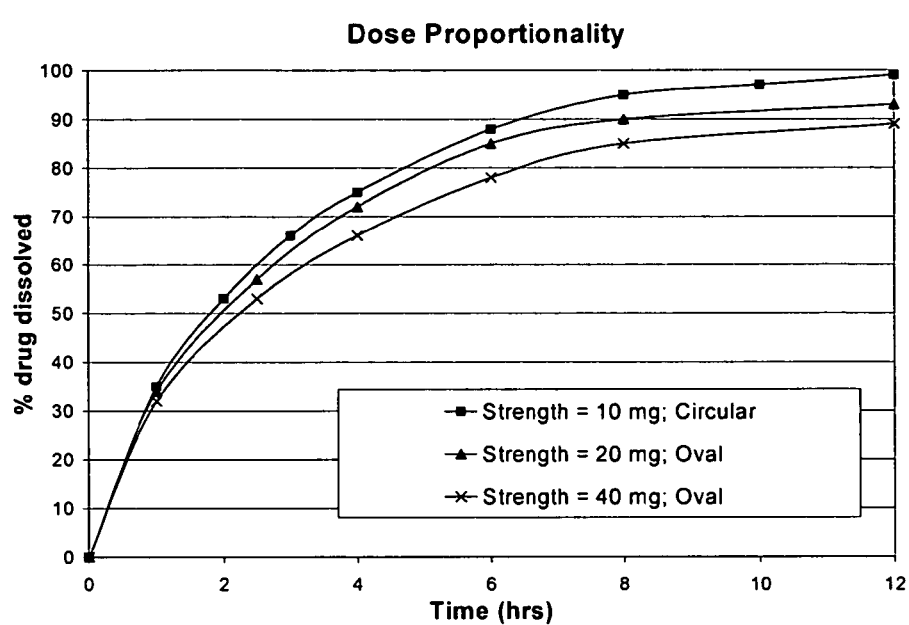
FIG. 8 shows the dose proportionality of drug dissolution over time (hours) for 10 mg (X data points), 20 mg (circular data points), and 40 mg (diamond data points) modified release memantine tablets. The 10 mg tablet is a circular shaped tablet, whereas the 20 mg and 40 mg tablets are oval shaped tablets. The shape of the tablet is critical to obtain the desired diffusion characteristics.

10 mg as compared to 40 mg formulations do not have proportional dissolution rates, i.e., 40 mg is slower than 10 mg. Note that the area to volume ratios are kept constant. In the erosion/diffusion type matrix system, it is important to keep this parameter constant to provide same erosion and diffusional flux. The dose proportionality data, shown in FIG. 8, demonstrate the varied rates. In FIG. 8, the 10 mg tablet is circular shape, and the 20 mg and 40 mg tablets are oval shaped tablets. The shape of the tablets is critical to achieve the desired diffusion characteristics.

Example 4

Modified Release Memantine

The present example demonstrates exemplary 6 hour and 12 hour release formulations of memantine hydrochloride.

40 mg (6 hour) formulations with total 300 to 600 mg fill weight were developed. The total weight was 200 mg for "6 Hour" formulation used in the pharmacokinetic study. The study optimized flow and compression properties of the tablet formulation. A series of batches were prepared with varying amount of lactose monohydrate as filler to study its effect on flow and compression properties. The specific objectives of this series of batches are as follows:

To study the effect of level of lactose monohydrate on the powder flow and compression properties, 400 mg, 500 mg and 600 mg tablet weight.

To study the effect of increase in amount of lactose on dissolution profiles, 400 mg, 500 mg and 600 mg tablet weight.

To study the effect of tablet shape on dissolution profile: circular and oval.

To investigate if the formulations are dose proportional at higher levels of lactose at 400 mg and 600 mg tablet weight.

To study the effect of storage conditions on the product performance.

The following Table shows the 6 hour formulations:

TABLE 7

| Item | A | B | C | D |
|---|---|---|---|---|
| Memantine HCl | 40 | 40 | 40 | 40 |
| Synchron KF | 130 | 130 | 130 | 130 |
| Lactose Monohydrate | 112 | 206 | 300 | 394 |
| Cab-O-Sil ® | 3 | 4 | 5 | 6 |
| Talc | 13.5 | 18 | 22.5 | 27 |
| Mg stearate | 1.5 | 2 | 2.5 | 3 |
| Total | 300 | 400 | 500 | 600 |

These lots were subdivided further. The reasons for subdivision are given in the table below.

TABLE 8

| Sublots | Shape | Dimension | Tablet weight (mg) | Strength (mg) | Hardness (kP) | Purpose of experiment |
|---|---|---|---|---|---|---|
| A | Circular | 11/32" | 300 | 40 | 10.6-12.8 | |
| BA | Circular | 11/32" | 400 | 40 | 9.5-15.9 | To test dose |
| BB | Circular | 11/32" | 200 | 20 | 10.2-11.8 | proportionality at |
| BC | Circular | 5/16" | 100 | 10 | 3.6-4.6 | lower fill wt |
| BD | Oval | 0.296" × 0.57" | 400 | 40 | 11.8-12.3 | Effect of tablet shape on 40 mg |
| CA | Circular | 7/16" | 500 | 40 | 3.7-4.8 | Effect of tablet |
| CB | Circular | 7/16" | 500 | 40 | 12.1-12.6 | hardness |
| CC | Circular | 7/16" | 500 | 40 | 19.1-19.6 | |
| DA | Circular | 7/16" | 600 | 40 | 11.7-13.5 | To test dose |
| DB | Circular | 11/32" | 300 | 20 | 11.0-12.8 | proportionality at |
| DC | Circular | 5/16" | 150 | 10 | 8.2-9.7 | Higher fill wt |

The powder properties of the final blends for compression were evaluated. During compression, excellent powder flow through the hopper was visually observed. The following Table presents the results of powder testing.

TABLE 9

| Lot # | Compressibility | Flowability Index |
|---|---|---|
| A | 12 | 57.5 |
| B | 10 | 58.0 |
| C | 10 | 62.0 |
| D | 15 | 59.0 |

The results above indicate that when the level of lactose was increased from 112 to 394 mg (Tablet weight from 300 mg to 600 mg), there was no significant change in the powder properties. For all the studied blends, the flow and compression properties are good.

The final tablets for each sublots had good hardness and friability values.

The effect of different types of lactose and the final weight on compression processes and dissolution was also studied. The current formulation study was executed to optimize compression process, flow and compression properties of the tablet formulation. A series of batches were prepared with varying amount of lactose, both grades anhydrous and monohydrate. The following Table details the formulations.

TABLE 10

| Item | A | B | C | D | E |
|---|---|---|---|---|---|
| Memantine HCl | 40 | 40 | 40 | 40 | 40 |
| Synchron KF | 130 | 130 | 130 | 130 | 130 |
| Lactose Monohydrate | 18 | 65 | 112 | — | — |
| Lactose Anhydrous | — | — | — | 65 | 112 |
| Cab-O-Sil | 2 | 2.5 | 3 | 2.5 | 3 |
| Talc | 9 | 11.25 | 13.5 | 11.25 | 13.5 |
| Mg stearate | 1 | 1.25 | 1.5 | 1.25 | 1.5 |
| Total weight/tablet | 200 | 250 | 300 | 250 | 300 |

All weights in mg

Figure 9:
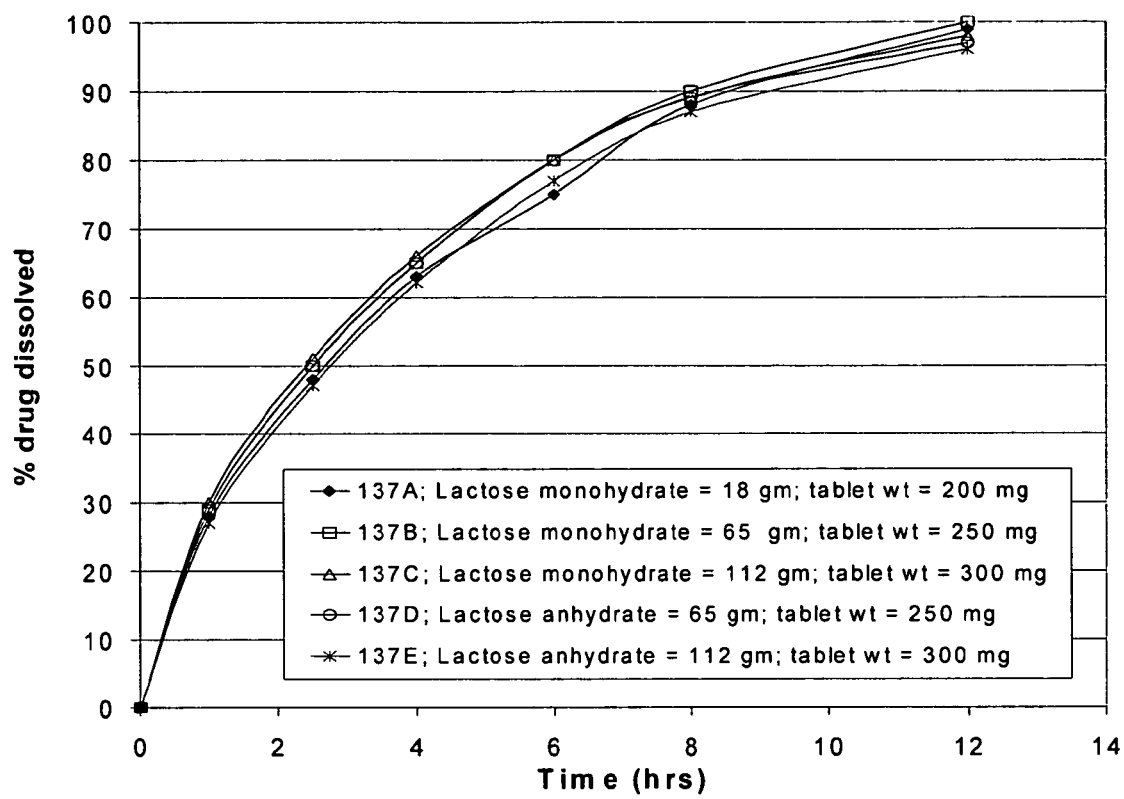
FIG. 9 presents the dissolution data as percent drug dissolved over time (hours) for using monohydrate and anhydrate forms of lactose in 40 mg modified release memantine tablets.

No significant differences in compressibility were observed between blend with lactose monohydrate compared to those with the anhydrate. The dissolution data are shown in FIG. 9. The data show no significant difference between the dissolution profiles for monohydrate and anhydrate forms of lactose. Increase in amount of lactose does not affect the release rate. It is concluded that release rate is dependent on the amount of Synchron KF for these formulations.

With respect to the flow and compression properties of memantine HCl, Synchron KF and lactose, it was observed that memantine itself has poor flow properties and flowability index is 23.5. This was attributed to the needle shaped particles of the drug. The flow property of lactose (both forms) was visually observed to be excellent. Microscopic examination revealed that the lactose monohydrate particles are larger and are more spherical in shape. The anhydrate yielded irregular shape agglomerates. Based on these results, the monohydrate form is preferred.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed:

1. A modified release solid oral dosage form, comprising
   (a) between about 2.5% w/w and about 20.0% w/w of memantine hydrochloride;
   (b) between about 68% w/w and about 77% w/w of hydroxypropyl methyl cellulose;
   (c) between about 6.9% w/w and about 15% w/w of lactose monohydrate;
   (d) between about 0.8% w/w and about 1.3% w/w of fumed silica;
   (e) between about 3.0% w/w and about 5.0% w/w of talc; and
   (f) between about 0.9% w/w and about 1.1% w/w of magnesium stearate; wherein the dissolution rate of memantine hydrochloride of more than about 80% is achieved after about 12 hours.

2. A modified release solid oral dosage form, comprising:
   (a) between about 5% w/w and about 35% w/w of memantine hydrochloride;
   (b) between about 54% w/w and about 65% w/w of hydroxypropyl methyl cellulose;
   (c) between about 7% w/w and about 24% w/w of lactose monohydrate;
   (d) between about 0.8% w/w and about 1.3% w/w of fumed silica;
   (e) between about 3.0% w/w and about 5.0% w/w of talc; and (f) between about 0.4% w/w and about 0.6% w/w of magnesium stearate; wherein the dissolution rate of memantine hydrochloride of more than about 80% is achieved after about 6 hours.

3. A modified release solid oral dosage form, comprising:
(a) between about 5% w/w and about 35% w/w of memantine hydrochloride;
(b) between about 54% w/w and about 65% w/w of hydroxypropyl methyl cellulose;
(c) between about 7% w/w and 40% w/w of microcrystalline cellulose;
(d) between about 0.8% w/w and about 1.3% w/w of fumed silica;
(e) between about 3.0% w/w and about 5.0% w/w of talc; and
(f) between about 0.4% w/w and about 0.6% w/w of magnesium stearate; wherein the dissolution rate of memantine hydrochloride of more than about 80% is achieved after about 6 hours.

4. A modified release solid oral dosage form, comprising:
(a) between about 5% w/w and about 35% w/w of memantine hydrochloride;
(b) between about 54% w/w and about 65% w/w of hydroxypropyl methyl cellulose;
(c) between about 7% w/w and 40% w/w of dicalcium phosphate;
(d) between about 0.8% w/w and about 1.3% w/w of fumed silica;
(e) between about 3.0% w/w and about 5.0% w/w of talc; and
(f) between about 0.4% w/w and about 0.6% w/w of magnesium stearate; wherein the dissolution rate of memantine hydrochloride of more than about 80% is achieved after about 6 hours.

5. The modified release solid oral dosage form of claim 1 wherein said modified release solid oral dosage form is a tablet.

6. The modified release solid oral dosage form of claim 2 wherein said modified release solid oral dosage form is a tablet.

7. The modified release solid oral dosage form of claim 3 wherein said modified release solid oral dosage form is a tablet.

8. The modified release solid oral dosage form of claim 4 wherein said modified release solid oral dosage form is a tablet.

* * * * *